(12) United States Patent
Lee

(10) Patent No.: US 7,722,655 B2
(45) Date of Patent: May 25, 2010

(54) ALOPECIA HEALING APPARATUS USING LASER AND LED

(75) Inventor: Hon-Kyo Lee, Seoul (KR)

(73) Assignee: Pros International Co., Ltd., Seoul (KR)

( * ) Notice: Subject to any disclaimer, the term of this patent is extended or adjusted under 35 U.S.C. 154(b) by 1037 days.

(21) Appl. No.: 10/565,471

(22) PCT Filed: Oct. 17, 2003

(86) PCT No.: PCT/KR03/02176

§ 371 (c)(1),
(2), (4) Date: Jan. 20, 2006

(87) PCT Pub. No.: WO2005/016454

PCT Pub. Date: Feb. 24, 2005

(65) Prior Publication Data

US 2006/0247742 A1   Nov. 2, 2006

(30) Foreign Application Priority Data

Aug. 13, 2003   (KR) .................. 10-2003-0056022

(51) Int. Cl.
*A61N 5/06* (2006.01)
(52) U.S. Cl. .......................... 607/88; 607/89
(58) Field of Classification Search .............. 607/88–89
See application file for complete search history.

(56) References Cited

U.S. PATENT DOCUMENTS

| | | | | |
|---|---|---|---|---|
| 3,659,180 A | * | 4/1972 | Urbush | 320/115 |
| 3,967,372 A | * | 7/1976 | Beck et al. | 30/34.1 |
| 4,732,834 A | * | 3/1988 | Honda et al. | 430/84 |
| 4,924,541 A | * | 5/1990 | Inagaki | 5/652.1 |
| 6,450,941 B1 | * | 9/2002 | Larsen | 600/14 |
| 6,739,016 B2 | * | 5/2004 | Bigio | 15/160 |

(Continued)

FOREIGN PATENT DOCUMENTS

JP   2002-315840   10/2002

(Continued)

*Primary Examiner*—Roy D Gibson
*Assistant Examiner*—Kaitlyn E Helling
(74) *Attorney, Agent, or Firm*—Jae Y. Park; Kile Goekjian Reed & McManus

(57) ABSTRACT

Disclosed is an alopecia healing apparatus. The alopecia healing apparatus has a case provided at a first end thereof with a handle section, and a second end thereof with a massage section having a plurality of massage protrusions, a light radiating section including a plurality of LEDs, which arc regularly aligned behind the massage protrusions of the case in equidistance, a laser radiating section aligned in the case corresponding to the massage section so as to radiate low-level laser beam, a vibration device installed in the case so as to vibrate the case, a control section including a microcomputer for controlling operations of the light radiating section, the laser radiating section and the vibration device, and a power source for supplying power to the light radiating section and the laser radiating section. The alopecia healing apparatus radiates low-level laser beam and optical pulses of the LEDs onto the scalp, so that the hair-root cells are activated, thereby promoting hair growth. Due to optical pulse of the LEDs and the vibration massage of the vibration device, the scalp is stimulated, so laser beam and drugs are effectively absorbed into the scalp.

8 Claims, 3 Drawing Sheets

U.S. PATENT DOCUMENTS

| | | | |
|---|---|---|---|
| 2002/0173780 A1* | 11/2002 | Altshuler et al. | 606/9 |
| 2003/0093915 A1* | 5/2003 | Pearl et al. | 34/96 |
| 2004/0006332 A1* | 1/2004 | Black | 606/9 |

FOREIGN PATENT DOCUMENTS

| | | |
|---|---|---|
| JP | 2003-144561 | 5/2003 |
| KR | 2002-0012969 | 2/2002 |
| KR | 2002-0289133 | 9/2002 |
| WO | WO 02/102228 | 12/2002 |

* cited by examiner

ALOPECIA HEALING APPARATUS USING LASER AND LED

TECHNICAL FIELD

The present invention relates to an alopecia healing apparatus capable of healing or preventing alopecia, and more particularly to an alopecia healing apparatus using a laser and an LED for promoting hair growth while preventing hair loss by activating hair-root cells through radiating laser beam of the laser and optical pulses of the LED towards the hair-root cells.

BACKGROUND ART

In general, a low-level laser treatment (LLLT) is widely used in the world as a curative means, in which low-level laser beam is radiated onto a skin, so DNA of the skin receives stimulation, so that protein synthesis is increased and a cell division in the skin is activated, thereby causing a quick circulation of the blood, reproducing a damaged skin tissue, and effectively curing an ulcer of the skin.

That is, when low-level laser beam is radiated onto a human body, blood vessels of the human body are expanded and the circulation of the blood is improved, thereby curing the damaged cell tissue as a normal state. In addition, when low-level laser beam is radiated onto acupuncture points of the human body, the acupuncture points are stimulated so that a pain in the skin and muscle is removed and the affected part of the human body is cured.

Although the low-level laser treatment was established in the year 1895 A.D., it has been widely spread in the world from the year 1989 A.D. due to a treatise "photobiological reaction" written by Dr. Tiina Karu, who was a professor of a Russia scientific academy technology center. According to the Tiina Karu's treaties, low-level laser beam stimulates and activates cell functions. After the treaties of Dr. Tiina Karu, the low-level laser treatment has been widely studied and developed in U.S.A, Europe, Japan, Russia and etc, and is now used as an effective curative means in various medical treatment fields. Through various studies and clinical demonstrations, it has become clear that the low-level laser treatment is effectively adapted for anti-inflammation, anti-inflammatory activity, thrombolysis, biological stimulation, and tissue reproduction. In particular, the low-level laser treatment effectively recovers immunity.

In addition, low-level laser beam radiated onto a scalp causes a quick circulation of the blood in the scalp and activates hair-root cells, thereby promoting hair growth with curing hair loss.

DISCLOSURE OF THE INVENTION

Therefore, the present invention has been made in view of the above-mentioned problems, and it is an object of the present invention to provide an alopecia healing apparatus for promoting hair growth while preventing hair loss by activating hair-root cells through radiating low-level laser beam and far-infrared ray optical pulse on to a scalp by using a laser and an LED with stimulating the scalp through a vibration massage such that low-level laser and drugs are easily penetrated into the scalp.

According to an aspect of the present invention, there is provided an alopecia healing apparatus comprising: a case provided at a first end thereof with a handle section, and a second end thereof with a massage section having a plurality of massage protrusions; a light radiating section including a plurality of LEDs, which are regularly aligned behind the massage protrusions of the case in equidistance; a laser radiating section aligned in the case corresponding to the massage section so as to radiate low-level laser beam; a vibration device installed in the case so as to vibrate the case; a control section including a microcomputer for controlling operations of the light radiating section, the laser radiating section and the vibration device; and a power source for supplying power to the light radiating section and the laser radiating section.

BRIEF DESCRIPTION OF THE DRAWINGS

The foregoing and other objects, features and advantages of the present invention will become more apparent from the following detailed description when taken in conjunction with the accompanying drawings in which.

BEST MODE FOR CARRYING OUT THE INVENTION

Reference will now be made in detail to the preferred embodiments of the present invention.

Figure 1:
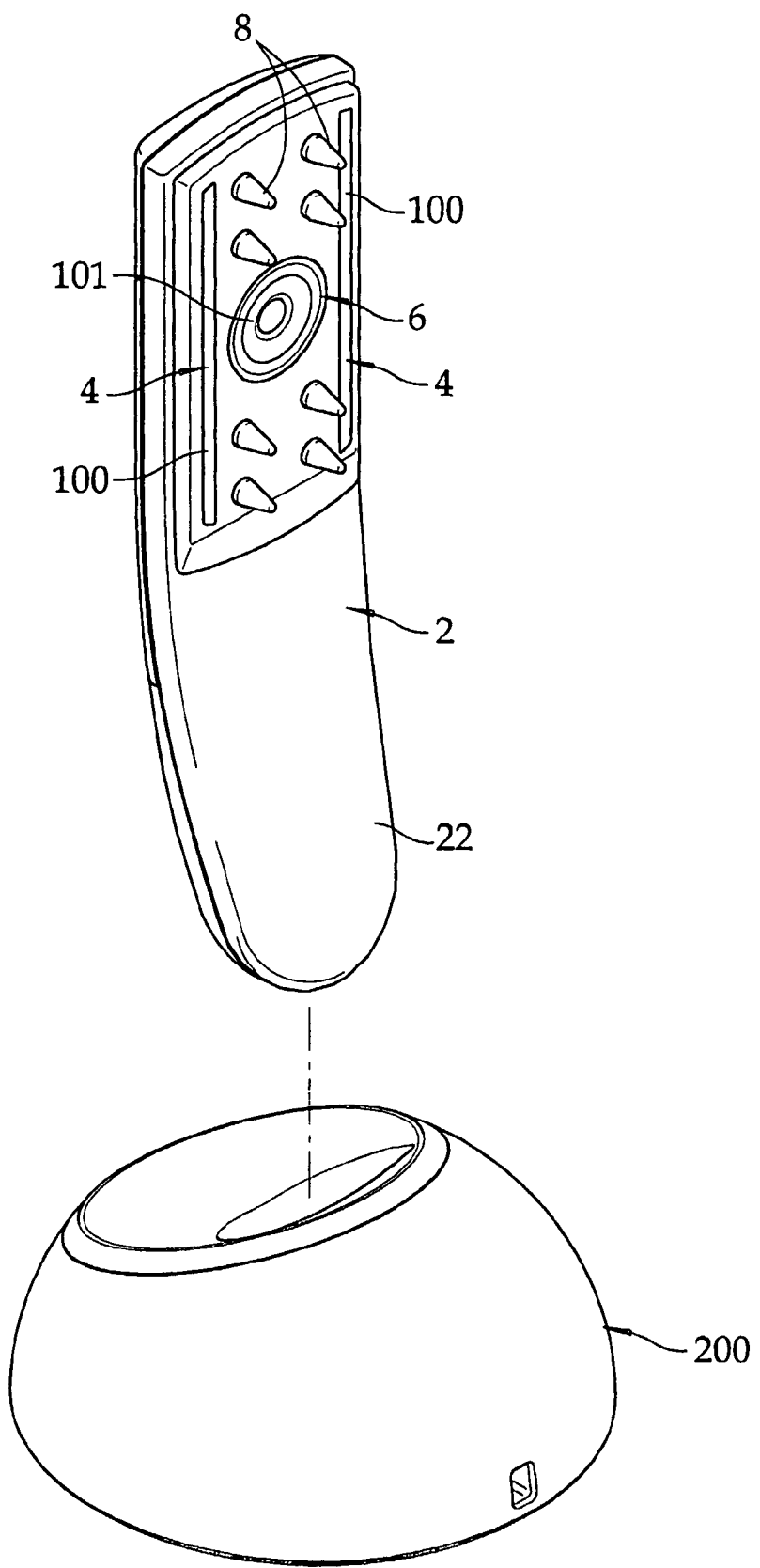
FIG. 1 is a perspective view showing an alopecia healing apparatus using a laser and an LED according to one embodiment of the present invention.
Figure 2:
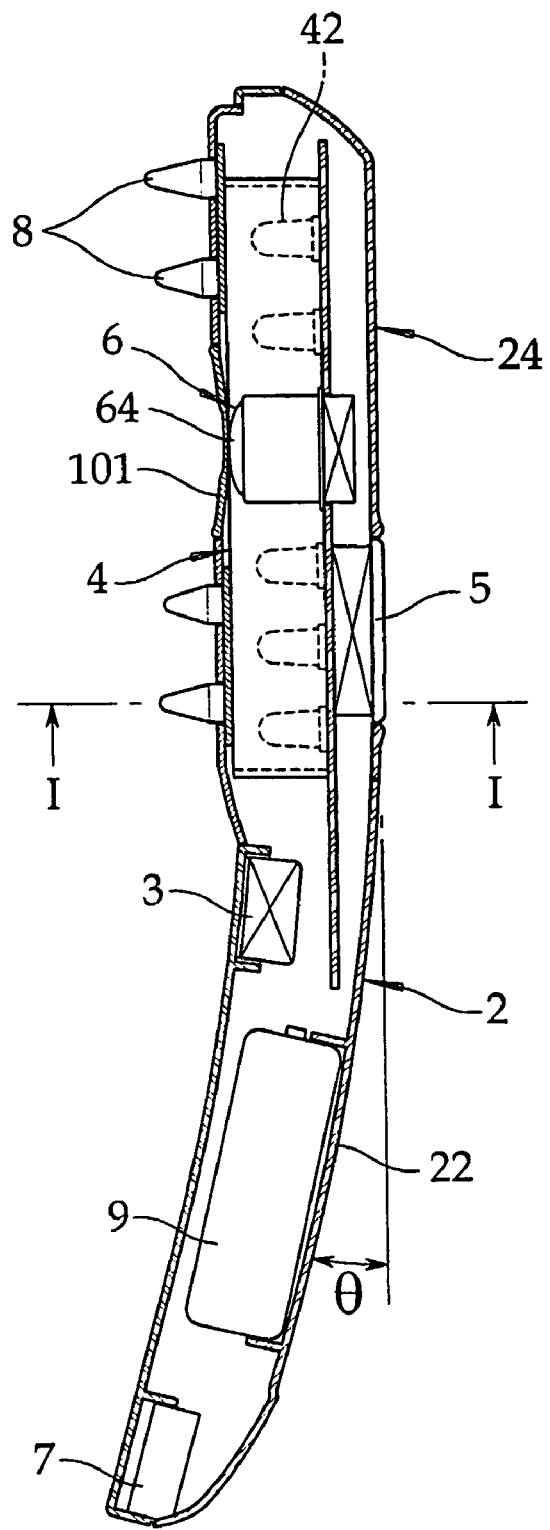
FIG. 2 is a side sectional view showing an alopecia healing apparatus using a laser and an LED according to one embodiment of the present invention.
Figure 3:
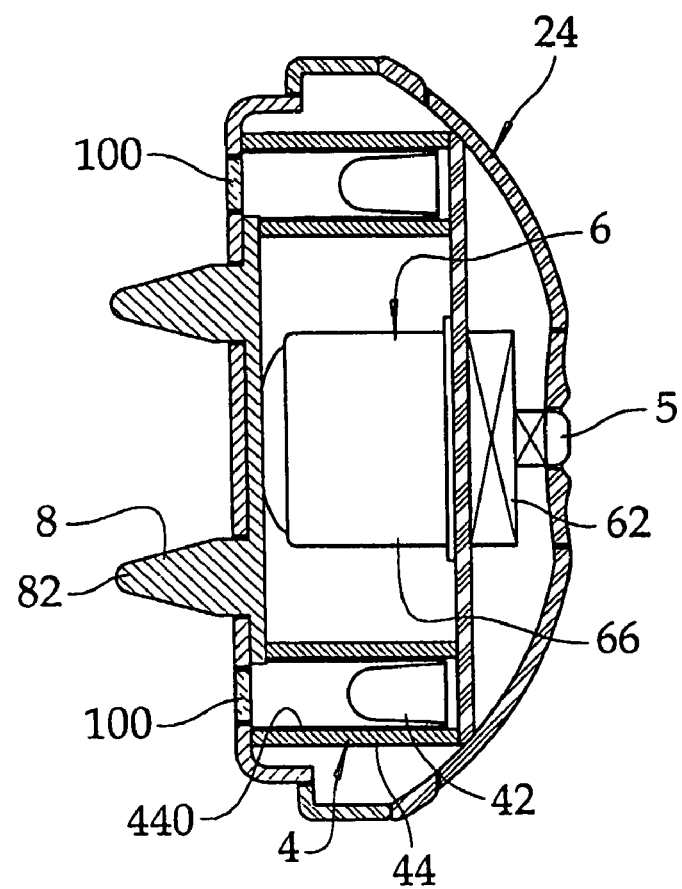
FIG. 3 is a front sectional view showing an alopecia healing apparatus using a laser and an LED according to one embodiment of the present invention.

FIG. 1 is a perspective view showing an alopecia healing apparatus using a laser and an LED according to one embodiment of the present invention, FIG. 2 is a side sectional view showing the alopecia healing apparatus using the laser and the LED according to one embodiment of the present invention, and FIG. 3 is a front sectional view showing the alopecia healing apparatus using the laser and the LED according to one embodiment of the present invention.

As shown in FIGS. 1 to 3, the alopecia healing apparatus has a case 2 provided at one end thereof with a handle section 22 and at the other end with a massage section 24 having a plurality of massage protrusions 8. The handle section 22 is inclined from the massage section 24 at an angle of 15° so as to enlarge a contact area between the massage section 24 and a scalp.

The massage protrusions 8 are formed in the massage section 24 to provide a massage effect to the scalp and to allow a user to comb user's hair by using the massage protrusions 8. The massage protrusions 8 are made of soft synthetic resin in order to allow the user to feel pleasant when combing the user's hair or when massaging the user's scalp. To this end, it is preferable to round a tip 82 of each massage protrusion 8.

In addition, in order to allow the massage protrusions 8 to effectively make contact with the scalp having a curvature, the length of the massage protrusions 8 is gradually increased from a center to upper and lower directions thereof. That is, uppermost and lowest protrusions 8 have the longest length.

A light radiating section 4 is provided to radiate far-infrared ray. The light radiating section 4 includes a rectangular substrate, a plurality of LEDs 42 regularly aligned on the rectangular substrate in equidistance, and a light collecting section 44 surrounding the LEDs 42 for providing a light collecting effect. The light radiating section 4 is aligned behind the massage protrusions 8 of the massage section.

The light collecting section 44 is formed at an inner surface thereof with a Cr-coated reflecting film 440 in order to prevent light radiated from the LEDs 42 from being dispersed into an exterior with linearly and uniformly radiating light.

Generally, the LED radiates point-type light when a radiating distance is within a short distance, thereby lowering light radiating efficiency. However, according to the present invention, linear-type light is radiated from the LEDs 42 by surrounding the LEDs 42 using the light collecting section 44. That is, light radiated from adjacent LEDs 42 is interrupted with each other so that point-type light is offset each other and linear-type light is radiated through the light collecting section 44.

According to a preferred embodiment of the present invention, the LEDs 42 have wavelength about 630 to 660 nm, and brightness about 2000 to 4000 mcd.

A laser radiating section 6 includes a laser source 62 installed at a rear portion of a cylindrical member 66 and a lens section 64 installed at a front portion of the cylindrical member 66 in order to scatter laser beam radiated from the laser source 62. The laser radiating section is aligned behind a center of the massage section 24 of the case so as to radiate low-level laser beam onto the scalp.

Since linear-type laser beam radiated from the laser source 62 is scattered through the lens section 64, light is widely radiated so that the light radiating efficiency is improved.

The low-level laser beam is generated from a He—Ne laser device or a Ga—As semiconductor laser device.

The He—Ne laser device radiates He—Ne laser beam having wavelength about 630 to 660 nm and including 90% of He and 10% of Ne, thereby creating visible red light. However, green light can be generated depending on a structure of the He—Ne laser device.

The Ga—As semiconductor laser device radiates Ga—As laser beam having wavelength about 790 to 904 nm, thereby creating invisible near-infrared ray. The Ga—As semiconductor laser device can be oscillated at low voltage with superior oscillating efficiency, so a battery can be used for oscillating the Ga—As semiconductor laser device. In addition, an output of the Ga—As semiconductor laser device is varied from 1 mW to 400 mW, so it is useful when a low-level laser treatment is carried out.

Low-level laser beam can deeply penetrate into the skin without destructing skin cells, so it can promote a metabolism by activating an organism and stimulating an immune system. In addition, low-level laser beam simultaneously creates the photo-electronic reaction, photo-magnetic reaction, photodynamic reaction, photo-immunity reaction, and photo-enzyme reaction, so it is adapted for curing various ulcers, pains, limphedema, and dermatitis with improving the blood circulation. Since low-level laser beam can be generated at low voltage, the alopecia healing apparatus can be fabricated in a portable size.

Reference numerals 100 and 101 represent transmission windows of the light radiating section and the laser radiating section, respectively.

A vibration device 3 includes a vibrator motor capable of vibrating itself. The vibration device 3 stimulates the scalp by vibrating the massage protrusions 8 with a predetermined frequency, causing an excited state of the cell. Thus, laser beam, light and drugs are easily absorbed into the scalp.

A control section includes a microcomputer for controlling the light radiating section 4, the laser radiating section 6 and the vibration device 3 in a predetermined mode. The control section periodically varies pulses so as to stimulate the skin, thereby activating the cell.

According to the present invention, when an operating switch 5 is turned on, the vibration device 3 is operated so that the light radiating section 4 is repeatedly switched on/off for 30 seconds. After that, the light radiating section 4 continuously radiates light for 30 seconds. However, the above operating mode can be variously modified as required by a user.

A chargeable battery is installed in the case 2 in order to feed power from the power source 9 into the light radiating section 4, the laser radiating section 6 and the vibration device 3. A charge terminal 7 connected to the chargeable battery is provided at a lower end of the case 2.

In addition, the alopecia healing apparatus also has an adapter 200, which receives the case 2 in order to charge the chargeable battery. When charging the chargeable battery one time, the user can uses the alopecia healing apparatus for a predetermined time without separately feeding power thereto, so that the alopecia healing apparatus can be conveniently used regardless of places.

Hereinafter, the operation of the alopecia healing apparatus according to the present invention will be described.

Firstly, the user turns on the operating switch 5 after allowing the massage section 24 of the case 2 to make contact with the scalp. Thus, the vibration device 3 is operated so that the massage protrusions 8 are vibrated, thereby massaging the scalp.

At the same time, the light radiating section 4 and the laser radiating section 6 are operated. At this time, the light radiating section 4 is repeatedly switched on/off for 30 seconds, and then, continuously radiates for 30 seconds according to a predetermined operation mode. This cycle is continuously repeated.

Accordingly, cells of the scalp are efficiently excited due to the vibration massage function and the optical pulses of the light radiating section, so laser beam and drugs for curing the alopecia are effectively absorbed into the scalp.

INDUSTRIAL APPLICABILITY

As can be seen from the foregoing, according to the present invention, an alopecia healing apparatus according to the present invention radiates low-level laser beam and far-infrared ray onto the scalp by using the laser device and the LEDs, so that the hair-root cells are activated, thereby promoting hair growth. In addition, due to optical pulse of the LEDs and the vibration massage of the vibration device, the scalp is stimulated, so laser beam and drugs are effectively absorbed into the scalp.

While this invention has been described in connection with what is presently considered to be the most practical and preferred embodiment, it is to be understood that the invention is not limited to the disclosed embodiment and the drawings, but, on the contrary, it is intended to cover various modifications and variations within the spirit and scope of the appended claims.

The invention claimed is:

1. An alopecia healing apparatus comprising:
   a case provided at a first end thereof with a handle section, and a second end thereof with a massage section having a plurality of massage protrusions;
   a light radiating section including a plurality of LEDs, which are regularly aligned behind the massage protrusions of the case in equidistance;
   a laser radiating section aligned in the case corresponding to the massage section so as to radiate low-level laser beam;
   a vibration device installed in the case so as to vibrate the case;

a control section including a microcomputer for controlling operations of the light radiating section, the laser radiating section and the vibration device; and a power source for supplying power to the light radiating section, the laser radiating section and the vibration device, wherein the handle section is inclined from the massage section at an angle of 15 degrees so as to enlarge a contact area between the massage section and a scalp;

the massage protrusions are made of soft synthetic resin in order to allow a user to feel pleasant when combing a user's hair or when massaging a user's scalp, and a tip of each massage protrusion is rounded;

length of the massage protrusions is gradually increased from a center to upper and lower directions thereof so that uppermost and lowest protrusions have longest length;

the laser radiating section includes a laser source installed at a rear portion of a cylindrical member and a lens section installed at a front portion of the cylindrical member in order to scatter laser beam radiated from the laser source, low-level laser beam radiated from the laser source is widely scattered by means of the lens section, and the laser source and lens section are aligned in a direction of the length of the massage protrusions; and the power source includes a chargeable battery, a charge terminal is formed at a lower end of the case, and an adapter is provided to charge the chargeable battery by receiving the case therein.

2. The alopecia healing apparatus as claimed in claim 1, wherein the light radiating section is surrounded by a light collecting section formed at an inner surface thereof with a Cr-coated reflecting film in order to prevent light radiated from the LEDs having wavelength about 630 to 660 nm and brightness about 2000 to 4000 mcd from being dispersed into an exterior and in order to make linear-type light.

3. The alopecia healing apparatus as claimed in claim 1, wherein the vibration device includes a vibrator motor capable of vibrating itself.

4. The alopecia healing apparatus as claimed in claim 1, wherein low-level laser beam includes He—Ne laser beam having wavelength about 630 to 660 nm.

5. The alopecia healing apparatus as claimed in claim 1, wherein low-level laser beam includes Ga—As laser beam having wavelength about 790 to 904 nm.

6. The alopecia healing apparatus as claimed in claim 1, wherein low-level laser beam includes He—Ne laser beam having wavelength about 630 to 660 nm.

7. The alopecia healing apparatus as claimed in claim 1, wherein low-level laser beam includes Ga—As laser beam having wavelength about 790 to 904 nm.

8. An alopecia healing apparatus comprising:

a case provided at a first end thereof with a handle section, and a second end thereof with a massage section having a plurality of massage protrusions;

a light radiating section including a plurality of LEDs, which are regularly aligned behind the massage protrusions of the case in equidistance;

a laser radiating section aligned in the case corresponding to the massage section so as to radiate low-level laser beam;

a vibration device installed in the case so as to vibrate the case;

a control section including a microcomputer for controlling operations of the light radiating section, the laser radiating section and the vibration device; and a power source for supplying power to the light radiating section, the laser radiating section and the vibration device, wherein the handle section is inclined from the massage section at an angle of 15 degrees so as to enlarge a contact area between the massage section and a scalp;

the massage protrusions are made of soft synthetic resin in order to allow a user to feel pleasant when combing a user's hair or when massaging a user's scalp, and a tip of each massage protrusion is rounded;

the alopecia healing apparatus continuously repeats a cycle including a first step of repeatedly switching on/off the light radiating section for 30 seconds as a vibration device is operated and a second step of radiating light for 30 seconds by using the light radiating section;

length of the massage protrusions is gradually increased from a center to upper and lower directions thereof so that uppermost and lowest protrusions have longest length;

the laser radiating section includes a laser source installed at a rear portion of a cylindrical member and a lens section installed at a front portion of the cylindrical member in order to scatter laser beam radiated from the laser source, low-level laser beam radiated from the laser source is widely scattered by means of the lens section, and the laser source and lens section are aligned in a direction of the length of the massage protrusions; and the power source includes a chargeable battery, a charge terminal is formed at a lower end of the case, and an adapter is provided to charge the chargeable battery by receiving the case therein.

* * * * *